(12) United States Patent
Eltorai

(10) Patent No.: US 12,115,385 B2
(45) Date of Patent: Oct. 15, 2024

(54) ANTIMICROBIAL LIGHT-EMITTING DEVICE AND METHOD OF REDUCING CATHETER-ASSOCIATED URINARY TRACT INFECTIONS

(71) Applicant: Luminary, LLC, Marlborough, MA (US)

(72) Inventor: Adam E. M. Eltorai, Marlborough, MA (US)

(73) Assignee: Luminary, LLC, Marlborough, MA (US)

( * ) Notice: Subject to any disclaimer, the term of this patent is extended or adjusted under 35 U.S.C. 154(b) by 0 days.

(21) Appl. No.: 17/851,538

(22) Filed: Jun. 28, 2022

(65) Prior Publication Data

US 2022/0323787 A1  Oct. 13, 2022

Related U.S. Application Data

(63) Continuation-in-part of application No. 17/665,965, filed on Feb. 7, 2022, now Pat. No. 11,596,772.

(60) Provisional application No. 63/215,910, filed on Jun. 28, 2021, provisional application No. 63/146,697, filed on Feb. 7, 2021.

(51) Int. Cl.
*A61M 25/00* (2006.01)
*A61M 39/16* (2006.01)
*A61N 5/06* (2006.01)

(52) U.S. Cl.
CPC ....... *A61N 5/0624* (2013.01); *A61M 25/0017* (2013.01); *A61M 39/16* (2013.01); *A61N 5/0603* (2013.01); *A61N 2005/061* (2013.01); *A61N 2005/0661* (2013.01); *A61N 2005/0663* (2013.01)

(58) Field of Classification Search
CPC ............... A61N 5/0624; A61N 5/0603; A61N 2005/061; A61N 2005/0661; A61N 2005/0663; A61M 25/0017; A61M 39/16; A61M 25/02; A61M 2025/0019; A61M 2025/0266

See application file for complete search history.

(56) References Cited

U.S. PATENT DOCUMENTS

| | | | | |
|---|---|---|---|---|
| 10,105,512 | B1 * | 10/2018 | Brar | A61M 1/3661 |
| 2006/0004317 | A1 * | 1/2006 | Mauge | A61M 27/006 |
| | | | | 604/8 |
| 2006/0183987 | A1 * | 8/2006 | Murray | A61N 5/0624 |
| | | | | 600/322 |
| 2009/0012459 | A1 * | 1/2009 | Sobue | A61M 1/285 |
| | | | | 604/29 |
| 2009/0204185 | A1 * | 8/2009 | De Kok | A61N 5/0613 |
| | | | | 607/88 |
| 2009/0257910 | A1 * | 10/2009 | Segal | A61L 2/10 |
| | | | | 250/455.11 |
| 2010/0072399 | A1 * | 3/2010 | Street | A61L 2/10 |
| | | | | 250/492.1 |

(Continued)

FOREIGN PATENT DOCUMENTS

| | | | | |
|---|---|---|---|---|
| CA | 3155384 | A1 * | 4/2021 | A61L 2/10 |
| WO | WO-2014165854 | A1 * | 10/2014 | A61L 2/10 |

*Primary Examiner* — Adam Marcetich
(74) *Attorney, Agent, or Firm* — Armis IP Law, LLC

(57) ABSTRACT

An antimicrobial urinary catheter device comprising a circumferential array of safe, antimicrobial lights around a urinary catheter directed for disinfecting the distal urethra, urethral meatus, and adjacent indwelling urinary catheter.

18 Claims, 10 Drawing Sheets

(56) References Cited

U.S. PATENT DOCUMENTS

| | | | | |
|---|---|---|---|---|
| 2012/0203211 A1* | 8/2012 | Weadock | ............... | A61L 29/16 |
| | | | | 604/544 |
| 2014/0235942 A1* | 8/2014 | Hellstrom | ............ | A61B 1/0615 |
| | | | | 128/200.26 |
| 2015/0037201 A1* | 2/2015 | Armour | ................. | A61B 90/06 |
| | | | | 600/203 |
| 2015/0165185 A1* | 6/2015 | Cohen | ...................... | A61L 2/10 |
| | | | | 128/207.14 |
| 2015/0335774 A1* | 11/2015 | Gomez | ................. | F16M 11/08 |
| | | | | 250/454.11 |
| 2016/0361529 A1* | 12/2016 | Finch, Jr. | .............. | A61M 1/285 |
| 2018/0207304 A1* | 7/2018 | Asano | ................... | A61M 39/16 |
| 2018/0296709 A1* | 10/2018 | Mishkin | ................ | A61L 2/0047 |
| 2019/0192706 A1* | 6/2019 | Zaborsky | ................. | A61L 2/26 |
| 2019/0381203 A1* | 12/2019 | Zaborsky | .......... | A61M 16/0493 |
| 2020/0030473 A1* | 1/2020 | Sugimoto | ............ | A61N 5/0624 |
| 2020/0230272 A1* | 7/2020 | Foote | ...................... | A61L 2/24 |
| 2020/0324078 A1* | 10/2020 | Motley | ............. | A61M 25/0017 |
| 2021/0113819 A1* | 4/2021 | Kalorin | ............... | A61N 5/0624 |
| 2021/0205589 A1* | 7/2021 | Dong | ................ | A61M 25/1025 |
| 2021/0230021 A1* | 7/2021 | Bailey | .................... | C02F 1/325 |
| 2022/0118131 A1* | 4/2022 | Kumar | ................... | A61L 29/14 |
| 2022/0152243 A1* | 5/2022 | Koppen | .................... | A61L 2/10 |
| 2022/0265877 A1* | 8/2022 | Ehring | ..................... | A61L 2/26 |
| 2022/0322924 A1* | 10/2022 | Bak | ........................... | A61L 2/10 |

\* cited by examiner

US 12,115,385 B2

ANTIMICROBIAL LIGHT-EMITTING DEVICE AND METHOD OF REDUCING CATHETER-ASSOCIATED URINARY TRACT INFECTIONS

RELATED APPLICATIONS

This Patent Application claims the benefit under 35 U.S.C. § 119(e) of U.S. Provisional Patent App. No. 63/215,910, filed Jun. 28, 2021, entitled "ANTIMICROBIAL LIGHT-EMITTING DEVICES," and is a Continuation-in-Part (CIP) of U.S. patent application Ser. No. 17/665,965, filed Feb. 7, 2022, entitled "ANTIMICROBIAL LIGHT-EMITTING PERCUTANEOUS SITE DRESSING," which claims the benefit under 35 U.S.C. § 119(e) of U.S. Provisional Patent App. No. 63/146,697, filed Feb. 7, 2021, entitled "ANTIMICROBIAL LIGHT DRESSING DEVICE," incorporated herein by reference in entirety.

BACKGROUND

Healthcare providers often access treatment areas through the use of elongated devices that penetrate or pierce a physiological boundary, such as the skin/epidermal system, gastrointestinal, urinary, nasal and ocular, to name several. The penetration of a foreign member introduces a risk of adverse results from infection resulting from the artificial path created by the inserted foreign member. Particularly in a healthcare environment, where many therapeutic procedures utilize these foreign members, the risk of provider or hospital caused infections is prevalent.

Catheter-associated urinary tract infections commonly occur from bacterial entry into the bladder along the catheter in the urethra. Decreasing bacterial entry can reduce urinary tract infection.

SUMMARY

Configurations herein are based, in part, on the observation that therapeutic procedures and treatment often involve a foreign member for transfer of fluids or samples between the human patient body and a treatment source or testing facility. Unfortunately, conventional approaches often involve the use of a foreign member such as a needle, vessel or probe to cross an external bodily boundary to access various organ systems for used in patient care. Insertion or breach into the bodily region by these foreign members can form a path for pathogens such as bacteria and other microorganisms to cause infection. Accordingly, configurations herein substantially overcome the shortcomings of the infection risk presented by conventional foreign members by providing an antibacterial, antipathogen light source for illuminating or irradiating a treatment region defining an insertion point of epidermal, gastrointestinal, urinary, or oral breach by a foreign member used in the course of treatment.

Catheter usage for urinary tract intervention involves insertion of a catheter vessel for urethral engagement. An inserted catheter vessel or tube, even if sterile upon insertion, presents a path for pathogens into the urethra and bladder. A circumferential frame having an array of lights around a perimeter and directed for focusing on a central void for illuminating a catheter provides a barrier to passage of pathogens. The frame provides an antimicrobial and safe light emission having a wavelength of or around 222 nm far UVC or 405 nm visible blue light for eradicating any bacteria or pathogens prior to infiltration via the catheter vessel.

In the case of percutaneous breach, intravenous delivery of medication is an effective medium for medicinal treatment directly to blood or tissue, which allows the medication to be quickly delivered to a specific region. General bloodstream delivery avoids degradation that can occur by oral administration which must pass via the gastrointestinal barrier. Unfortunately, conventional approaches to percutaneous delivery, typically via a needle or similar insertion member, suffer from the shortcoming that they pose an infection risk from a breach of the natural dermal (skin) barrier which guards against infiltration of pathogens. Typically, an antimicrobial substance is applied around the insertion point of the needle, however such chemical based approaches generally have diminishing effects over time, and need repeated applications for continued effectiveness.

Accordingly, configurations herein substantially overcome the shortcomings of chemical and topical approaches by providing an antimicrobial light dressing device, system and method for a percutaneous treatment that bathes a treatment region around the percutaneous insertion with an antibacterial illumination source for preventing pathogens around the insertion from entering via the dermal puncture created by the insertion. The antimicrobial light dressing device combines a circumferential body centered around the insertion, and an arrangement of LEDs around the body that focus the light around the insertion and onto a therapeutic region of the insertion. An opening in the circumferential body has an articulated protrusion for offsetting a medicinal vessel such as an IV tube off the skin surface to avoid blocking light to an area under the vessel. The result is a 360 degree coverage of antimicrobial light around the percutaneous insertion as the medicinal vessel contacts the skin surface only at the insertion point in the center of the treatment region.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

A device for the dressing of wounds and insertion sites of percutaneous and drug delivery devices provides circumferential protection of a wound or insertion site of a percutaneous or drug delivery device. In particular, the device is an integrated dressing for vascular and non-vascular percutaneous medical devices (e.g., IV catheters, central venous lines, arterial catheters, dialysis catheters, peripherally inserted coronary catheters, mid-line catheter, drains, chest tubes, externally placed orthopedic pins, ventricular assist device drivelines, and epidural catheters) comprising an adhesive dressing and an antimicrobial light source, such as visible light, far UVC light, and any suitable electromagnetic emission of a therapeutically beneficial wavelength. The dressing device reduces infection risk from vascular and non-vascular percutaneous medical devices by providing sufficient tissue-safe antimicrobial light at a wound or insertion site.

Figure 1:
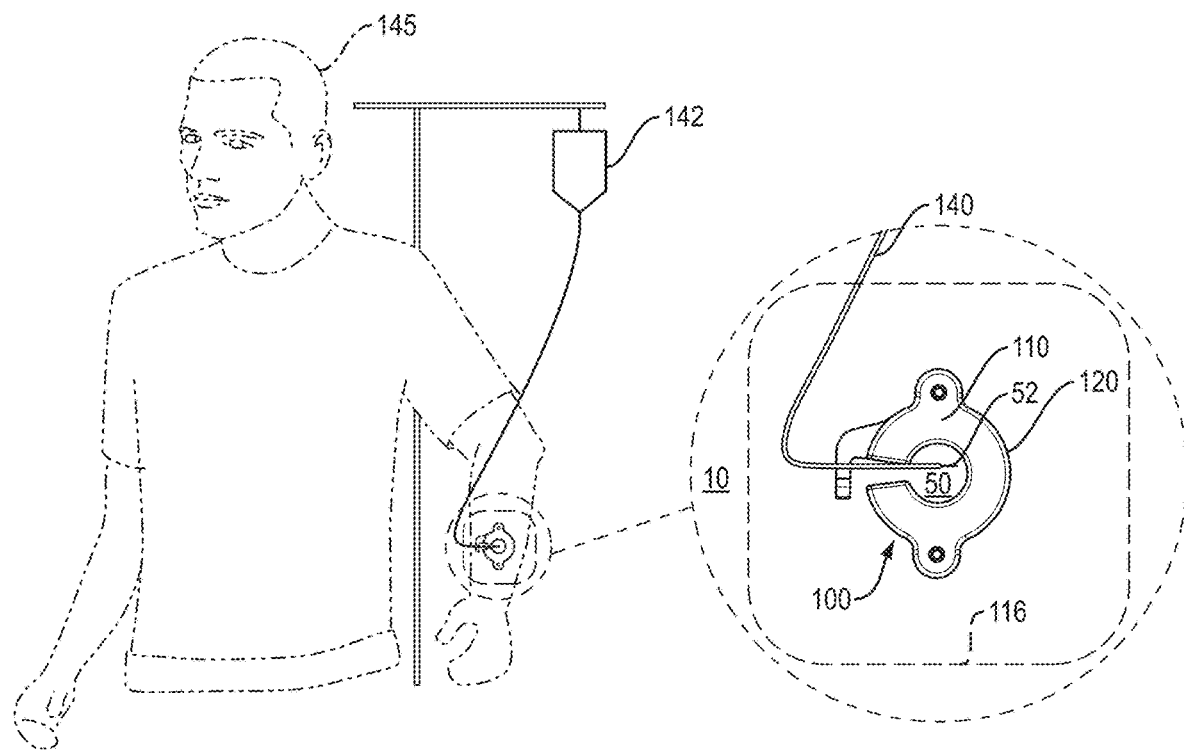
FIG. 1 is a context view of a medical treatment environment suitable for use with configurations herein.

FIG. 1 is a context view of a medical treatment environment suitable for use with configurations herein. Referring to FIG. 1, an antimicrobial epidermal device 100 includes a circumferential light-emitting body 110 configured for adhesion around a percutaneous insertion site 52 for directing therapeutic light at the percutaneous insertion site while permitting unobstructed passage of a medication vessel 140 to the percutaneous insertion site 52. The medication vessel emanates from a fluidic source 142 of medication or other liquid, such as an IV (Intravenous) bag. The percutaneous insertion site 52 defines a surrounding treatment region 50, typically on an arm of a patient 145 because of ease of IV access, however any suitable epidermal region may be selected for the percutaneous insertion site.

In the antimicrobial epidermal device 100, the circumferential body 110 is adapted for epidermal placement on the treatment region 50 of a larger epidermal surface 10. Placement is based on a central void 120 in the circumferential body for epidermal access and alignment generally over the insertion site 52. The circumferential body 110 includes an illumination source disposed for emitting a therapeutic light on the treatment region 50 defined by the central void 120. An adhesive member 116, such as a patch or bandage, adheres the circumferential body 110, vessel 140 and a percutaneous penetration member such as a needle to the epidermal area around the treatment region 50.

Figure 2:
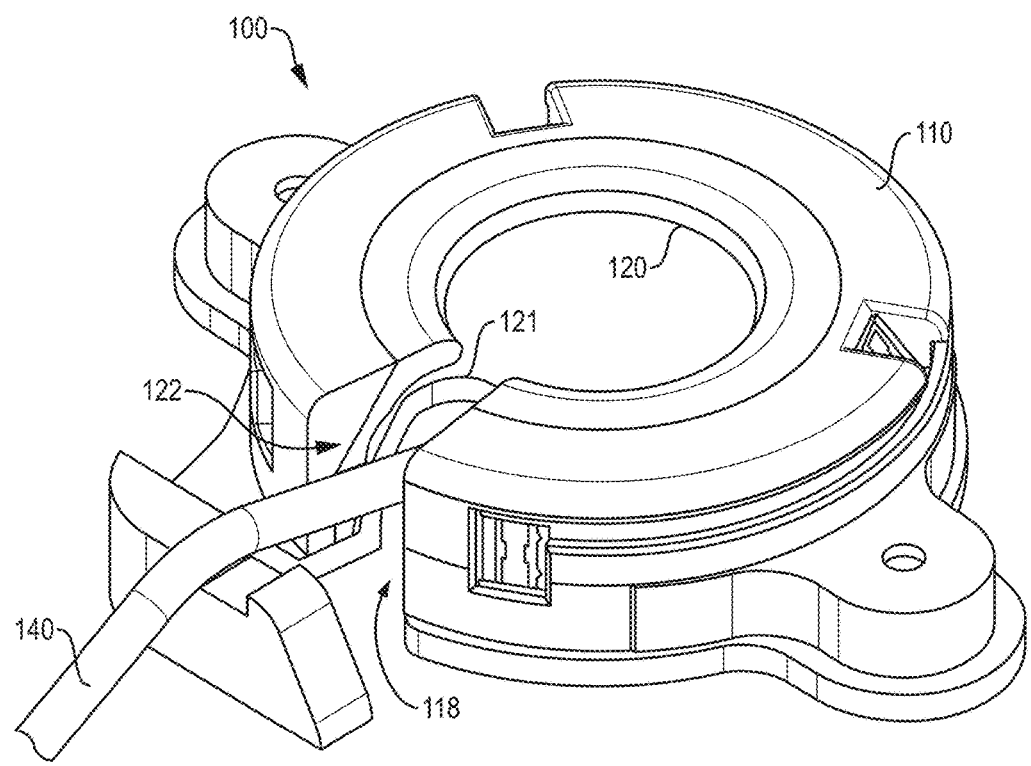
FIG. 2 is a perspective view of the medical device for antimicrobial light treatment of a percutaneous insertion site.

FIG. 2 is a perspective view of the medical device of FIG. 1 for antimicrobial light treatment around a percutaneous insertion site 52. FIG. 2 shows the central void 120 accessible by a vessel gap 122 in the circumferential body 110 for passage of the medication vessel 140 to a penetration or insertion member defining the insertion site 52. The treatment region 50 is defined by a radius around the insertion site roughly centered within the circumferential body. In the example of FIG. 2, the central void 120 remains covered by an insert 121 except at the vessel gap 122 for permitting vessel access into an illumination cavity 118.

Figure 3A:
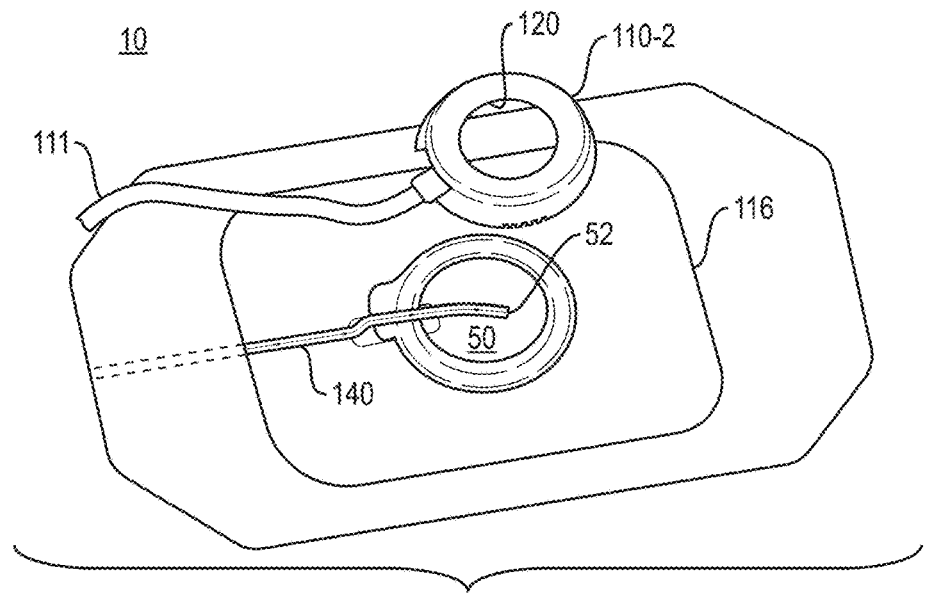
FIGS. 3A-3C show engagement of the device of FIG. 2 with a treatment region defined by the percutaneous insertion site.
Figure 3B:
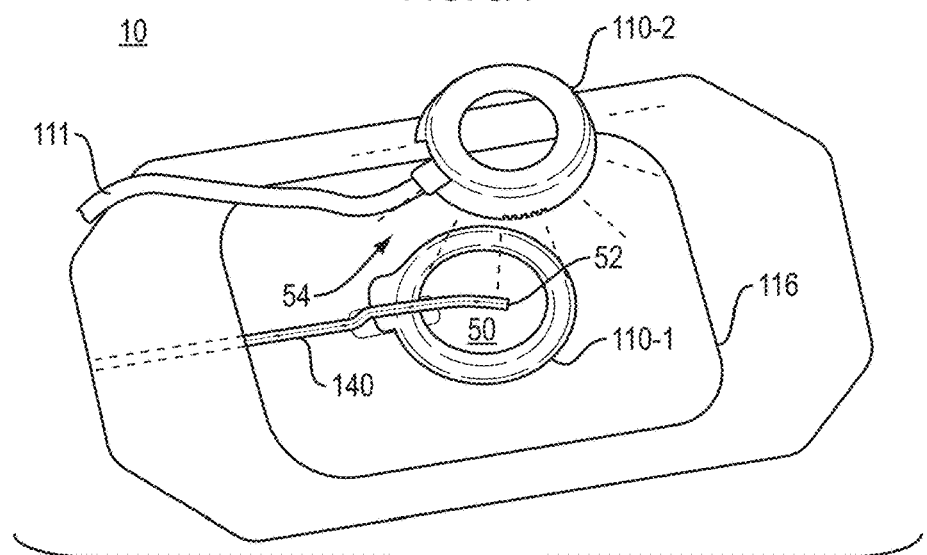
Figure 3C:
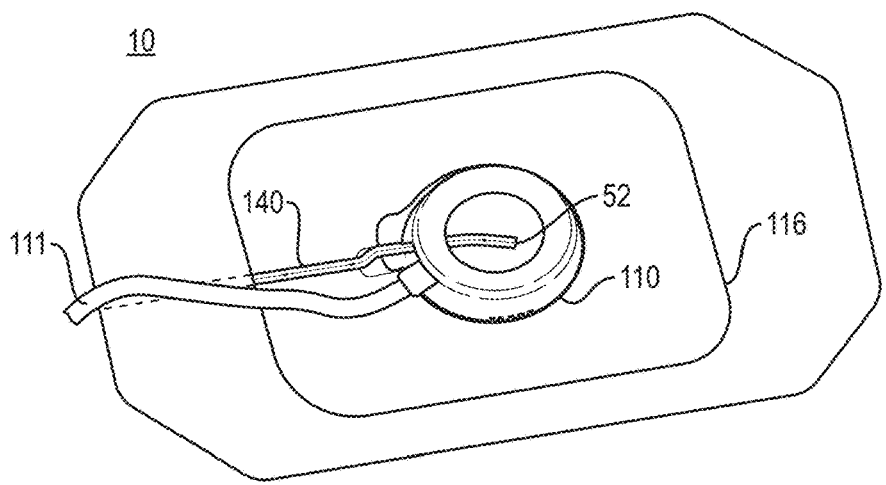

FIGS. 3A-3C show engagement of the device of FIG. 2 with a treatment region defined by the percutaneous insertion site. In a particular configuration, the device may be combined with an adhesive member 116 such as a sheet, patch or bandage for providing a system of secure attachment of the illumination source to the percutaneous insertion site. Referring to FIGS. 1-3C, the circumferential body 110 is disposed on an epidermal surface 10, in conjunction with an adhesive member 116. The adhesive member 116 has an adhesive attraction to the epidermal surface 10 and extends over the treatment region 50 and is disposed for securing the circumferential body 110 and a treatment vessel 140 directed to the central void 120. The adhesive member my include a securement or fixation dressing having adhesive and therapeutic or antimicrobial properties. The securement or fixation dressing is disposed between the circumferential body 110 and the epidermal surface 10. The circumferential body is therefore disposed in place by the underlying securement or fixation dressing/patch, and substantially centered around the insertion site.

The configuration of FIG. 3 shows a two-part configuration of the device. The circumferential body 110 further includes a distal layer 110-2 including a power connection 111 for powering an illumination source such as one or more LED elements and a proximate layer 110-1 having a translucent surface, in which the LED elements are disposed within the distal layer 110-2 for directing the therapeutic light onto the treatment region 50.

The proximate layer 110-1 engages with the adhesive member 116, which may be integrated as an adhesive whole or applied in separate phases. In the configuration of FIGS. 3A-3C, the adhesive member 116 may reside between the proximate layer 110-1 and distal layer 110-2. The adhesive member 116 secures the insertion member at the insertion site 52 alone with the medication vessel 140, shown in FIG. 3A. The treatment region 50 is defined by a radius around the dermal insertion site 52, where the insertion site 52 provides the dermal access for medical intervention through the skin by a sharp, piercing structure.

In FIG. 3B, the distal layer 110-2 approaches the secured, proximate layer 110-1. The distal layer 110-2 may already be emitting light 54 onto the treatment region 50. In FIG. 3C, the distal layer 110-2 engages the proximate portion 110-2 to form the full circumferential member 110, and encapsulates an illumination cavity, discussed further below.

Figure 4A:
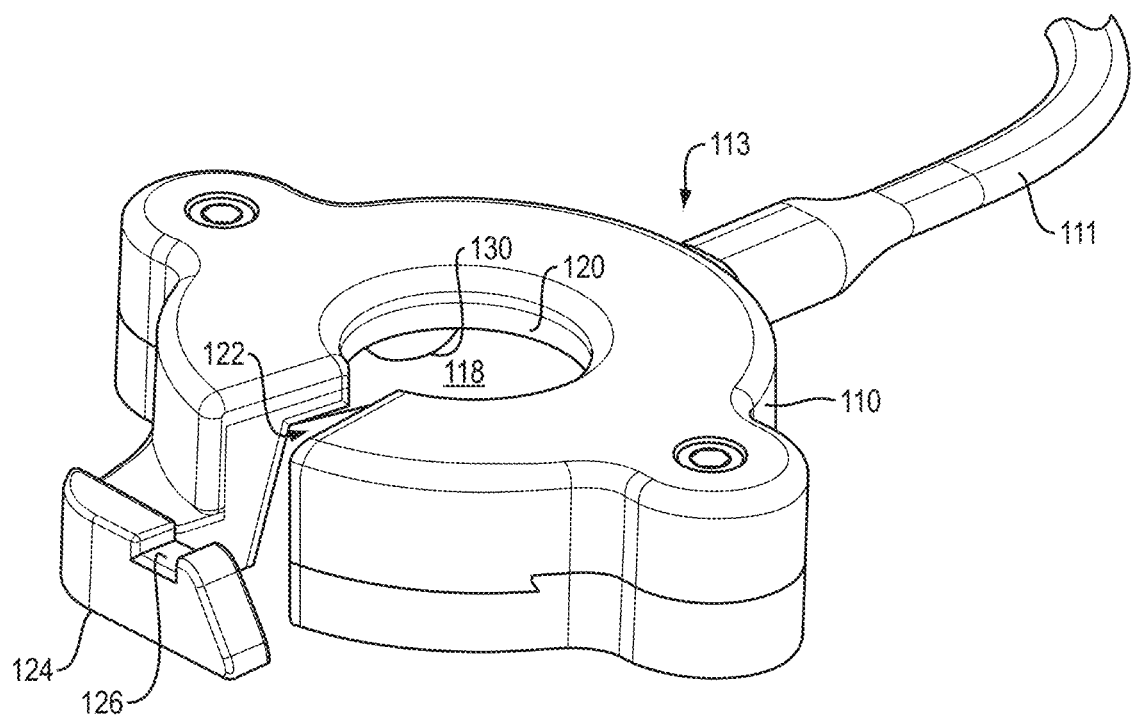
FIGS. 4A-4B show perspective views of a central void in the device of FIGS. 1-3c.
Figure 4B:
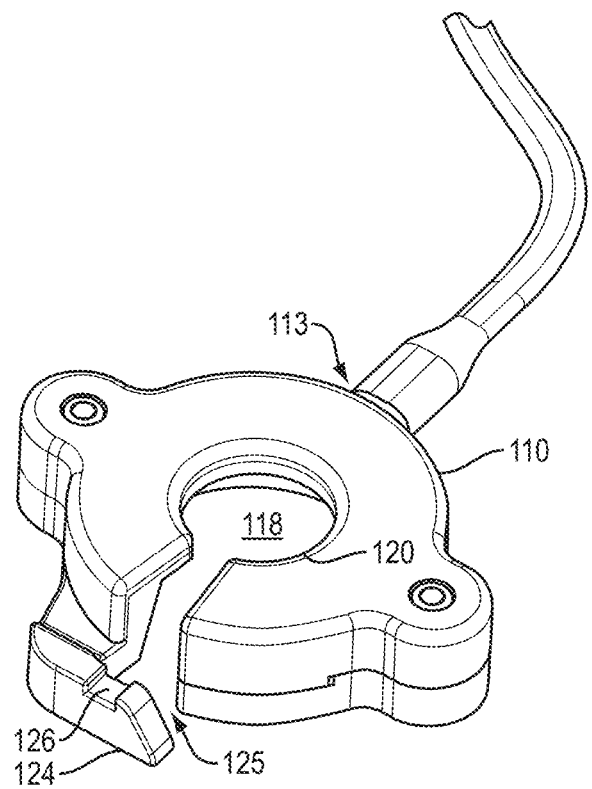

FIGS. 4A-4B show perspective views of a central void 120 in the device of FIGS. 1-3c. Referring to FIGS. 1-4B, upon adherence and proper administration, the circumferential body 110 adheres to the epidermal surface 10 with the central void 120 roughly centered on the insertion site 52. An illumination source 130 includes at least one LED element defining the illumination source, in which the LED element emits a wavelength based on an antimicrobial effect. The central void 120 has a size based on a treatment vessel 140 size and clearance over the insertion site 152. The treatment vessel 140 has an attachment to the insertion member such as a needle for a percutaneous insertion under the central void. The vessel extends through the vessel gap 122 and through the central void 120 or at least through the gap 122 and into the illumination cavity 118.

A power connection 113 receives the power supply 111 on the circumferential body 110. The power supply couples to the illumination source 130 and is adapted for receiving an electrical source for powering the illumination source, such as an external USB, batteries, AC or similar AC or DC source based on the electrical requirements of the illumination source 30. A discontinuity in the circumferential body defines the vessel gap 122 for accommodating the treatment vessel 140. The treatment vessel 140 couples to the percutaneous insertion member in the treatment region 50 under the central void 120. Routing of the treatment vessel 140 is provided by a protrusion 124 extending outward from the circumferential body. The protrusion 124 has an elevated surface 126 disposed away from the epidermal surface 10, such that the elevated surface 126 is adjacent the vessel gap 122 for directing the treatment vessel at an offset distance from the dermal surface 10. Elevation of the treatment vessel 140 above the skin avoids a shadow from the light and instead allows a shadowed region 125 to be reached by light from the illumination source 130 rather than being shaded or obscured by the vessel 140 from reaching the skin at the shadowed region.

Figure 5:
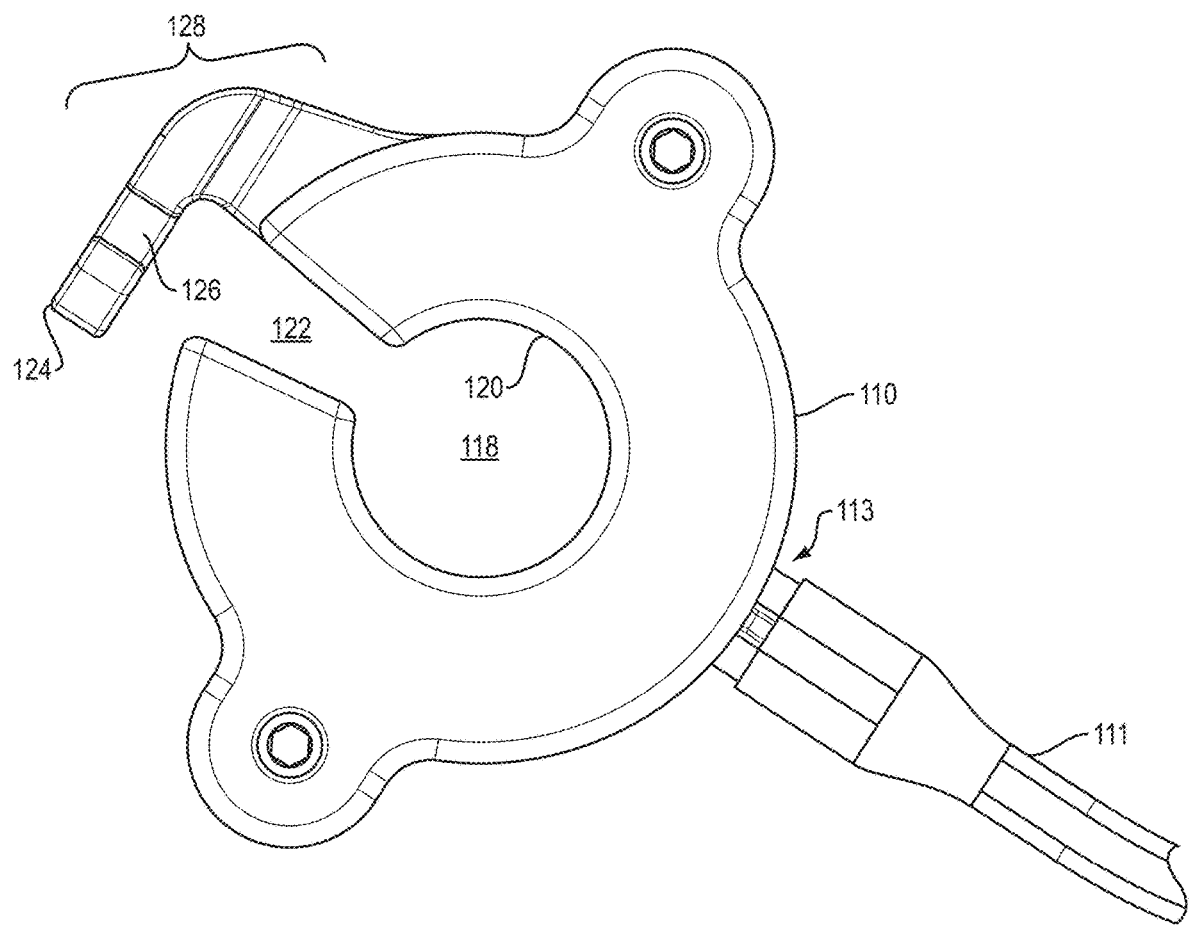
FIG. 5 shows a plan view of the device of FIGS. 1-4B.

FIG. 5 shows a plan view of the device of FIGS. 1-4B. Referring to FIGS. 1-5, the vessel gap 122 is an opening or passage in the circumferential body 110. A lateral extension 128 extends radially from the circumferential body 110 adjacent the vessel gap 122, and turns toward the gap 122 to provide the elevated surface 126 residing on the protrusion 124. The elevated surface 126 is disposed on a path towards the central void 120 for receiving a treatment vessel 140 disposed on the path for fluidic delivery to an insertion site 52 in the treatment region 50.

Figure 6:
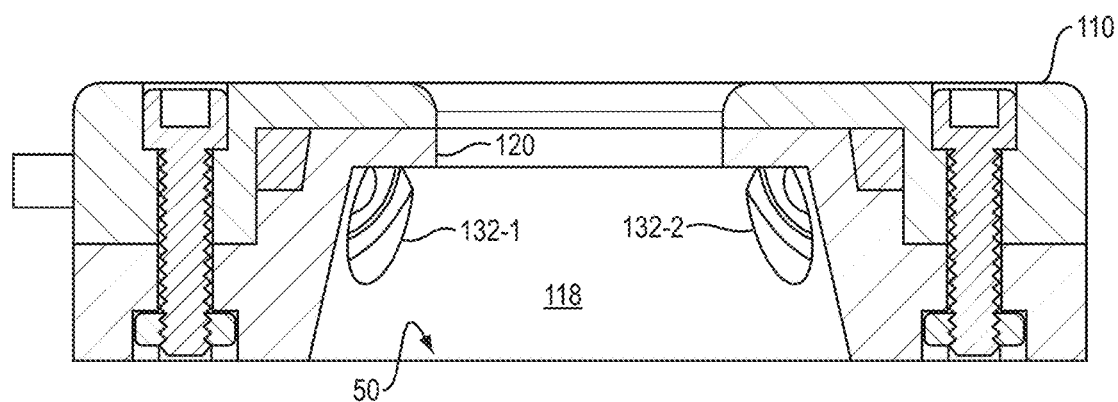
FIG. 6 shows a side, cutaway view of the central void and illumination cavity formed by the device of FIGS. 1-5.

FIG. 6 shows a side, cutaway view of the central void and light cavity formed by the device of FIGS. 1-5. Referring to FIGS. 1-6, a plurality of LED elements 132-1 . . . 132-2 (132 generally) surround the illumination cavity 118, although as few as 1 could be provided. In the example configuration, the plurality of LED elements 132 are disposed generally in a circle around the circumferential body 110, and fill the illumination cavity 118 with light focused on the treatment region 50. The inner surface of the circumferential body 110 and optional insert 121 are a light color and may be translucent to reflect and refract (distribute and target) as much if the light as possible around the illumination cavity 118 to fall on the treatment region 50. The antimicrobial light is therefore specifically targeted to fall on the treatment region defined by the percutaneous insertion and surrounding epidermal region, specifically within the illumination cavity 118 of the circumferential body 110.

Figure 7:
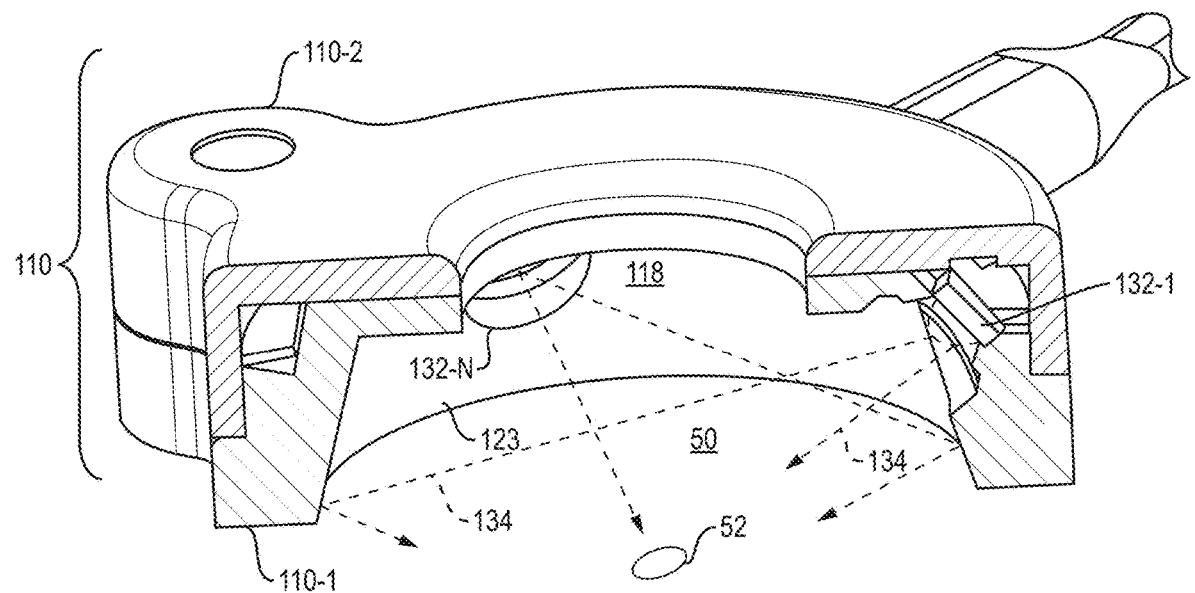
FIG. 7 shows a perspective view of the illumination cavity of FIG. 6.

FIG. 7 shows a perspective view of the light cavity of FIG. 6 as a cutaway from the circumferential body 110. Referring to FIGS. 1-7, the circumferential body 110 is disposed on a treatment region 50 and centered on or around an insertion site 52 of a percutaneous insertion member. One or more LED elements 132-N disposed on an inner surface 123 of the circumferential body bathe the illumination cavity 118 in light for directing the light directly on the treatment region 50 and also reflected and/or refracted around the inner surface 123 as shown by arrows 134. A light colored, translucent and/or reflective property of the inner surface 123 generally focuses direct and indirect light onto the treatment region 50 for eliminating harmful pathogens that may live on the skin surface around the insertion site 52.

Figure 8:
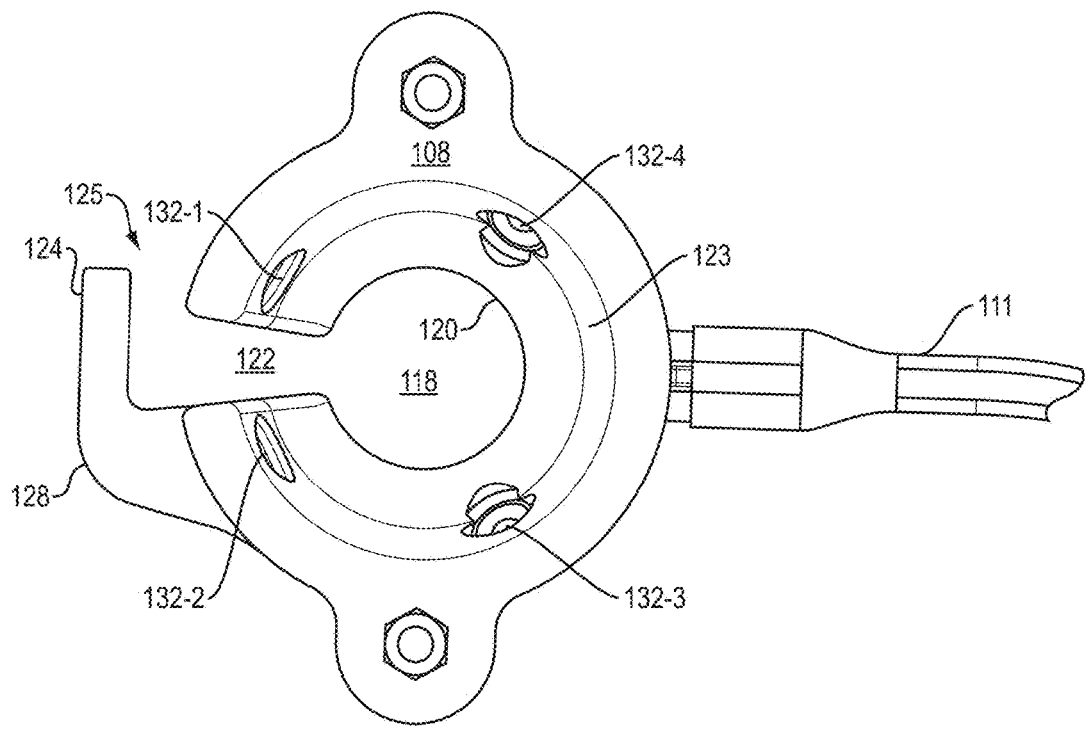
FIG. 8 shows a bottom view of the device of FIGS. 1-7.

FIG. 8 shows a bottom view of the device of FIGS. 1-7. Referring to FIGS. 7-8, FIG. 8 shows four LEDs 132-1 . . . 132-4 emanating from the inner surface 123, however any suitable number of LEDs may be provided based on the intensity and wavelength of the therapeutic light sought for irradiation. Any suitable propagated wavelength of the electromagnetic spectrum may be provided if an illumination element can be so equipped. The underside 108 rests on the dermal surface 10 at the treatment region, adhered by the adhesive member 116 as discussed above. The protrusion 124 has a bottom flush with the underside 128, and opens to define the illumination cavity 118. The lateral extension 128 is flush with the underside 128 for resting on the skin surface, and extends in an articulated manner for protrusion 124 to form the elevated surface 126 at the vessel gap 122.

Figure 9:
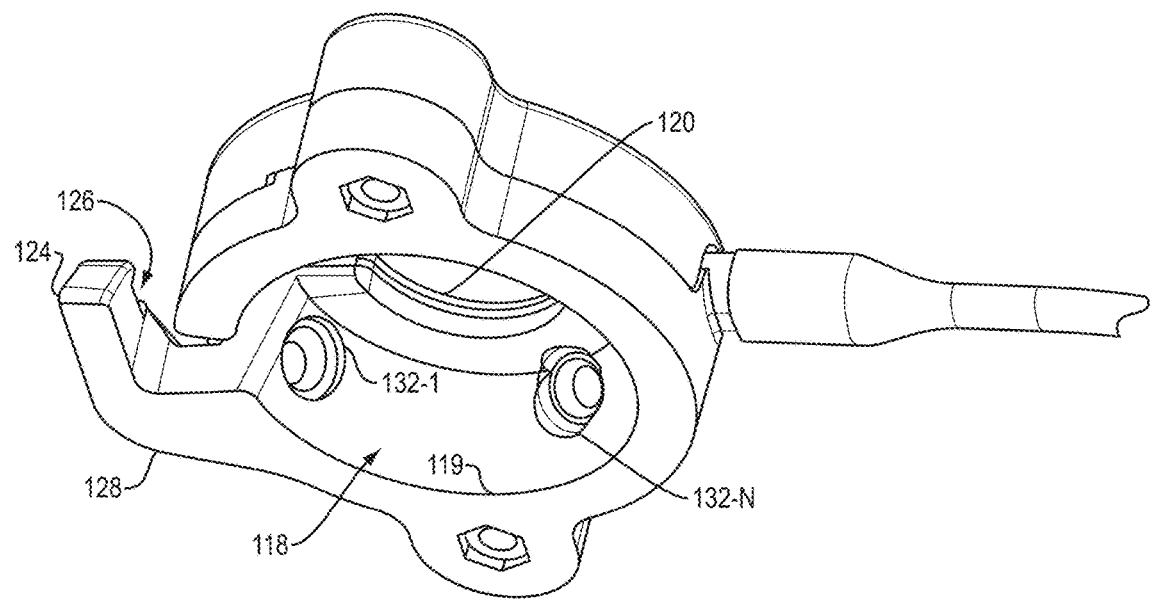
FIG. 9 shows an underside perspective view of the device and illumination/light cavity of FIGS. 6-8.

FIG. 9 shows an underside perspective view of the device and illumination cavity 118 of FIGS. 6-8. The illumination cavity 118 is based on a generally concave region under the central gap 120 and extending to an inner perimeter 119 of the circumferential body 110, with the vessel gap 122 allowing passage of the treatment vessel 140.

Figure 10:
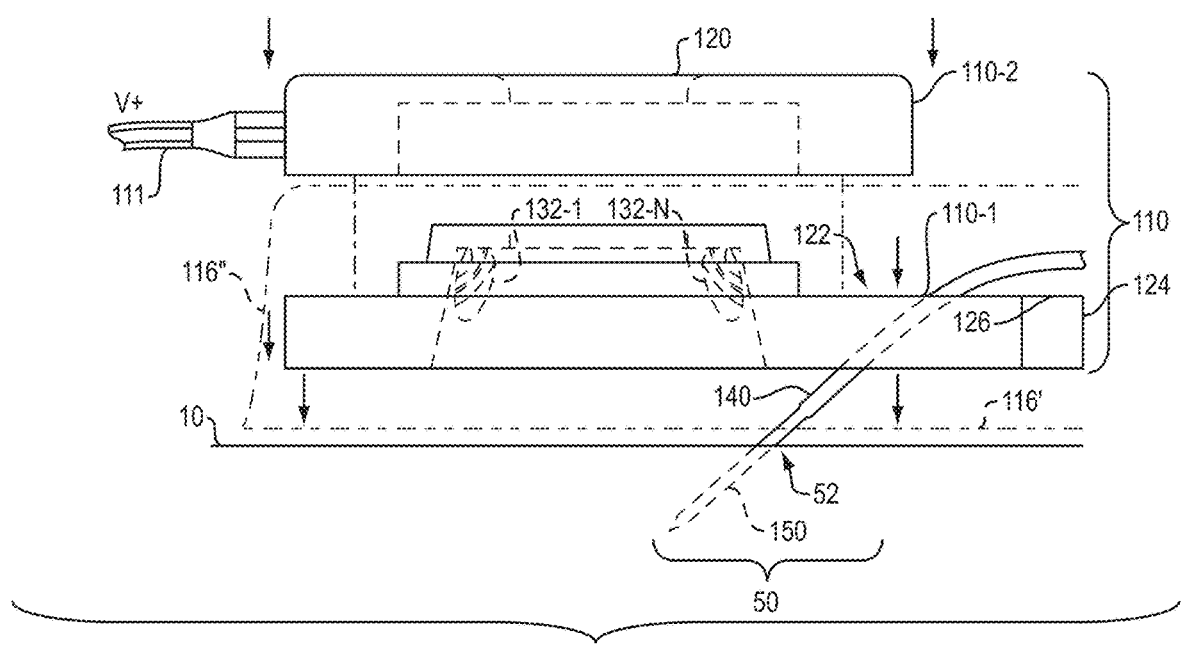
FIG. 10 shows a method of applying the antimicrobial light treatment of FIGS. 1-9.

FIG. 10 shows a method of applying the antimicrobial light treatment of FIGS. 1-9. Referring to FIGS. 1-10, a method for antimicrobial light treatment of a percutaneous insertion site as shown in FIG. 10 includes applying an adhesive member 116 to a treatment region 50 for securing a percutaneous insertion member in an insertion site. The percutaneous insertion member 150, such as a needle, is in fluidic communication with a medication vessel 140 for delivering medication, typically an IV line, infusion line or similar delivery system. The adhesive member 116 may adhere on the epidermal surface, shown as dotted line 116', or may be applied over the circumferential member 110, shown as dotted line 116". In the alternate configuration of FIGS. 3A-3B, the adhesive member 116" may reside between the proximate layer 110-1 and distal layer 110-2.

In either configuration, the circumferential body 110 is disposed onto the treatment region 52. The circumferential body 110 extends generally circular around a central void 120, and placement centers the central void around the insertion site so that the central void allows clearance for the medication vessel 140 and any uninserted portion of the rigid insertion member. The circumferential body 110 may be any suitable shape and size based on the treatment region 50 and the intensity of the illumination source 130 thereby irradiating the treatment region.

The circumferential body 110 includes a discontinuous portion defining the vessel gap 122, which may be continuous with the central void 120. In conjunction with placement of the circumferential body 110, the medication vessel is routed over the elevated surface 126 on the protrusion 124 extending from the circumferential body for permitting the vessel to extending through the vessel gap 122 above and out of contact with the skin surface. The treatment region 50 is illuminated from one or more LEDs (Light Emitting Diodes) 132 disposed on an inner surface of the circumferential body 110 for irradiating an illumination cavity 118 defined by the inner surface and the central void. The LEDs 132 or other illumination source irradiate the treatment region for maintaining an antimicrobial and sterile environment around the insertion site 50. This prevents pathogens from entering the patient along the insertion member 150.

In a particular configuration shown in FIGS. 3A-3C above, the circumferential body has multiple, engageable parts. A first, proximate layer 110-1 accompanies the insertion member 150. Disposing the circumferential body 110 further comprises disposing the proximate layer 110-1 by applying a proximate layer centered on the treatment region using the adhesive member 116, and engaging the distal layer 110-2 onto the proximate layer 116-1 by circumferentially aligning the distal layer with the proximate layer, the LEDs directed towards the illumination cavity. Any suitable adhesive, friction, interference and/or deformable (i.e. snap-fit plastic tab) mechanism may be employed for engaging the proximate 110-1 and distal 110-2 layers.

Figure 11:
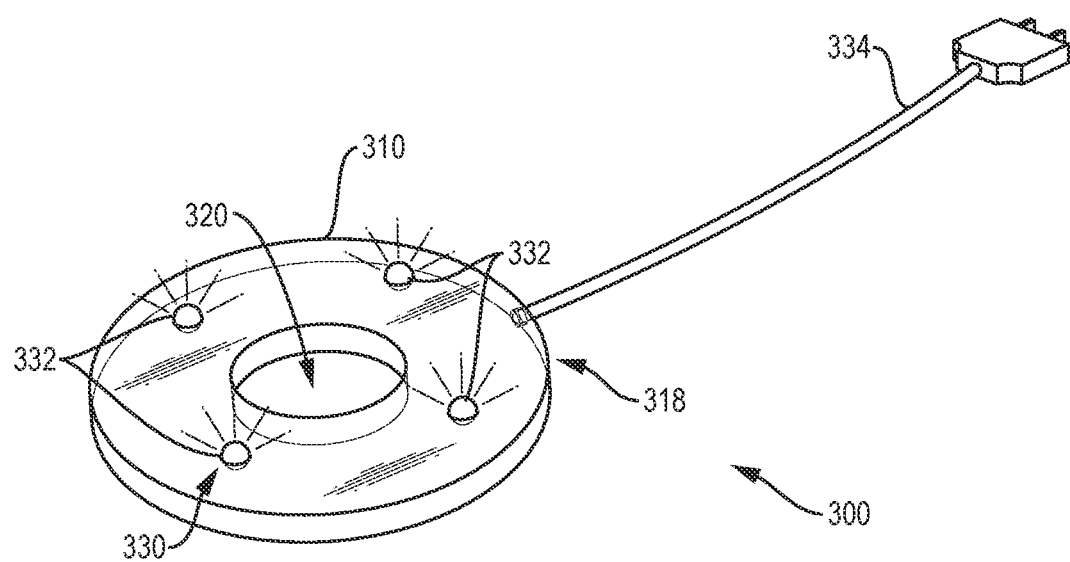
FIG. 11 shows an alternative configuration of the safety device for use with a urinary catheter.

FIG. 11 shows an alternative configuration of the safety device for use with a urinary catheter. Referring to FIGS. 1 and 11, an antibacterial catheter device 300 includes a circumferential frame 310 having an array 330 of lights around a perimeter 318 and directed for focusing on a central void 320 for illuminating a catheter. The antibacterial, antipathogenic catheterization safety device 300 orients the frame 310 and orifice 320 to receive the catheter, and directs the light from the array of lights 330 or other suitable illumination source, disposed on the frame 310, at the orifice 320. A connection 334 to a power supply is invoked to activate the illumination source, and may be a battery operated or plug (USB or similar) tethered connection. The light has predetermined wavelength having an ability to eradicate microorganisms; in a particular configuration, the illumination source includes one or more light emitting diodes (LEDs), each LED providing an antimicrobial and safe light emission having a wavelength substantially around 222 nm or 405 nm. A typical range might be 217-227 nm or 400-410 nm wavelength. To illuminate completely around the catheter, the circular frame 310 has a plurality of LEDs defining the illumination source, such that the LEDs circumferentially surround the circular frame at a perimeter or mid-radius on the frame for focusing axially along a length of the catheter.

Figure 12:
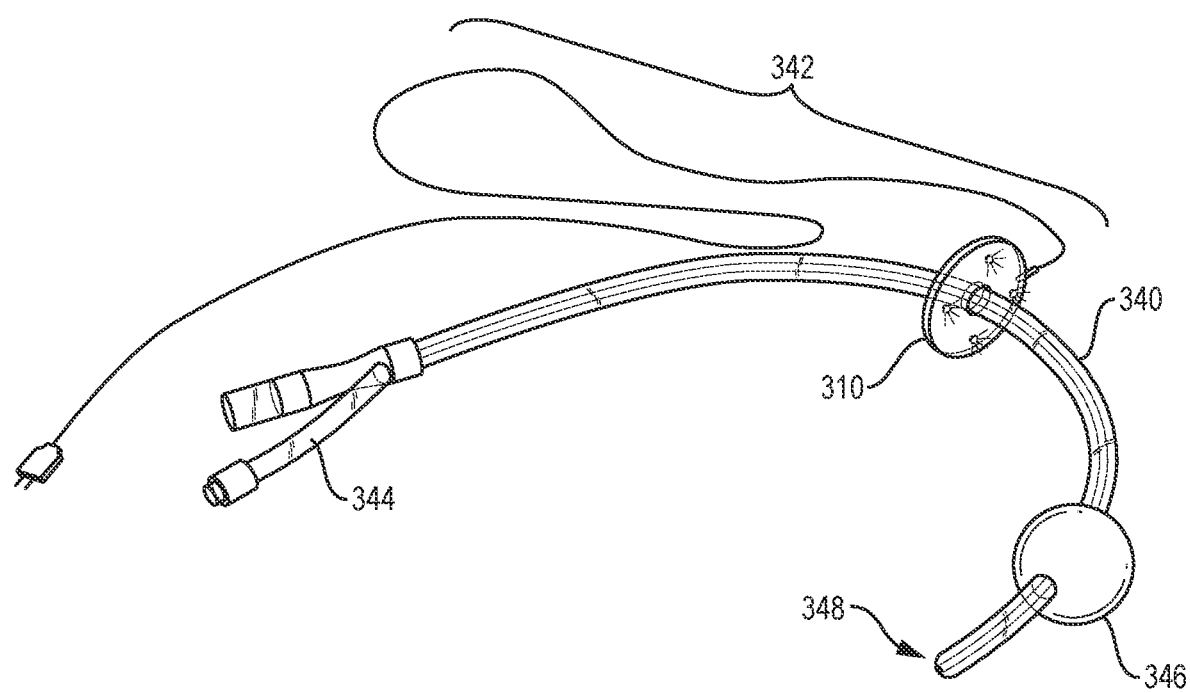
FIG. 12 shows the device of FIG. 11 engaged with a catheter set including a catheter vessel.

FIG. 12 shows the device of FIG. 11 engaged with a catheter set including a catheter vessel 340. Referring to FIGS. 11 and 12, the catheter device 300 takes the form of a slidable cuff, where the slidable cuff attaches the circular frame in a slidable engagement with the vessel 340 for disposing the circular frame adjacent an insertion site. Each of the plurality of LEDs 332 is arranged towards the central void for providing circumferential irradiation of the vessel 340 passing through the central void. In the example of FIGS. 11 and 12, the central void 320 has a size for slidable engagement with the vessel 340 of catheter tube 342, including a catheter connector 344 and expandable balloon 346 for expanding the urethra to allow insertion of the drainage end 348

Figure 13:
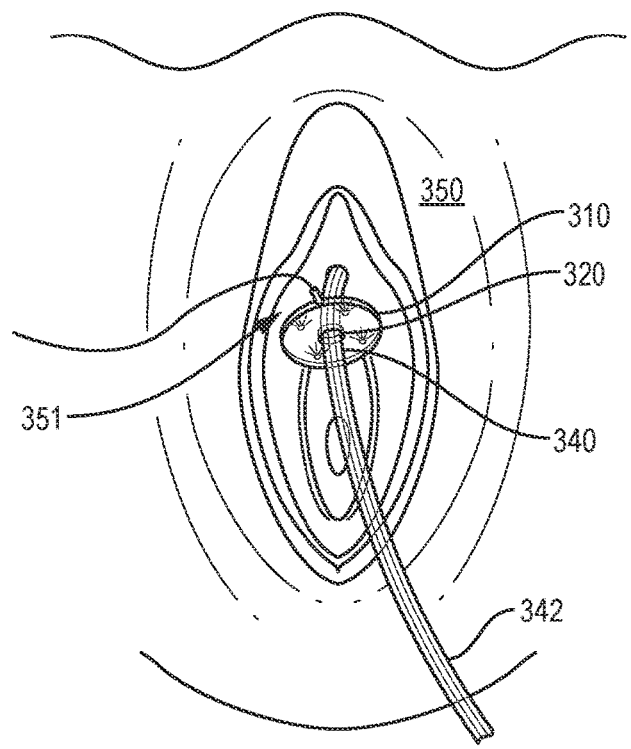
FIG. 13 shows the device of FIGS. 11 and 12 engaged in a treatment region.

FIG. 13 shows the device of FIGS. 11 and 12 engaged in a treatment region. The example configuration with a catheter involves fluidic engagement of the catheter with a treatment region 350 including a urethra and bladder of the patient. The antimicrobial urinary catheter device comprising a circumferential array of safe, antimicrobial lights around a urinary catheter directed for irradiating and disinfecting the treatment region 350 including the distal urethra, urethral meatus, and adjacent indwelling urinary catheter. The illumination source is disposed for irradiation of the vessel 340 passing through the central void 310 at the entry 351 or breach to the patient, typically in the genital region but may also be achieved by a lower abdominal insertion. The LEDs are specifically chosen to irradiate a light wavelength of 222 nm far UVC or 405 nm visible blue light, having antibacterial properties for eliminating pathogens, at the insertion region 350 to bathe the vessel 340 and surrounding area to eradicate a source of infection which might otherwise travel the surface 342 of the vessel 340 into vulnerable regions of the urethra and bladder.

Figure 14:
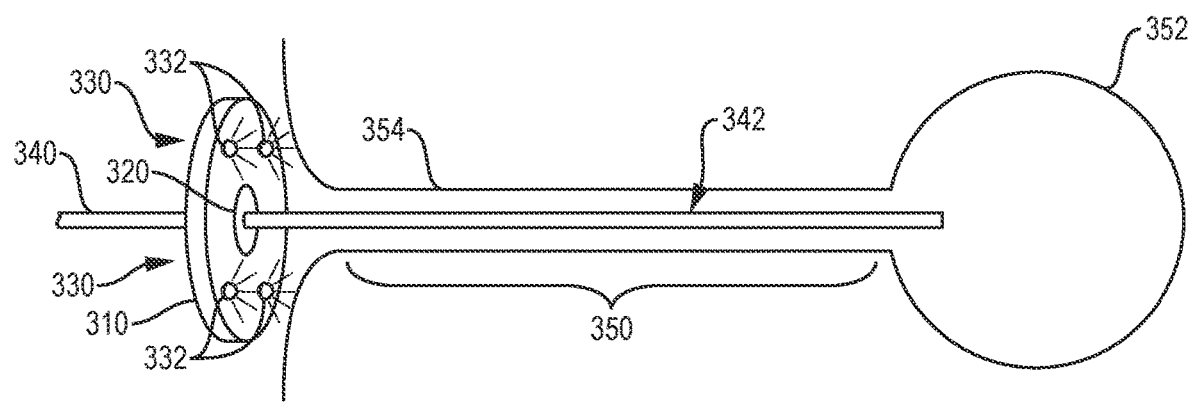
FIG. 14 shows a side view of the patient engaged device of FIG. 13.

FIG. 14 shows a side view of the patient engaged device of FIG. 13. Referring to FIGS. 11-14, a method for sterile insertion of a catheter includes engaging the circular frame 310 with the vessel 340 defining a catheter tube 342, where the frame has a central void 320 for passage of the vessel and an illumination source 330 for directing light of a predetermined therapeutic wavelength. Insertion disposes the catheter at a treatment region by insertion in a urethral path 354. The circular frame 310 is slidably adjusted along the vessel until it is adjacent the treatment region 350 for illuminating an insertion site 351. During catheter 342 insertion, a power source energizes the illumination source for irradiating the treatment region 350 with the light of the therapeutic wavelength, therefore blocking a path for pathogens that might otherwise reach the urethra region 354 and bladder 352 via the vessel 340.

Figure 15A:
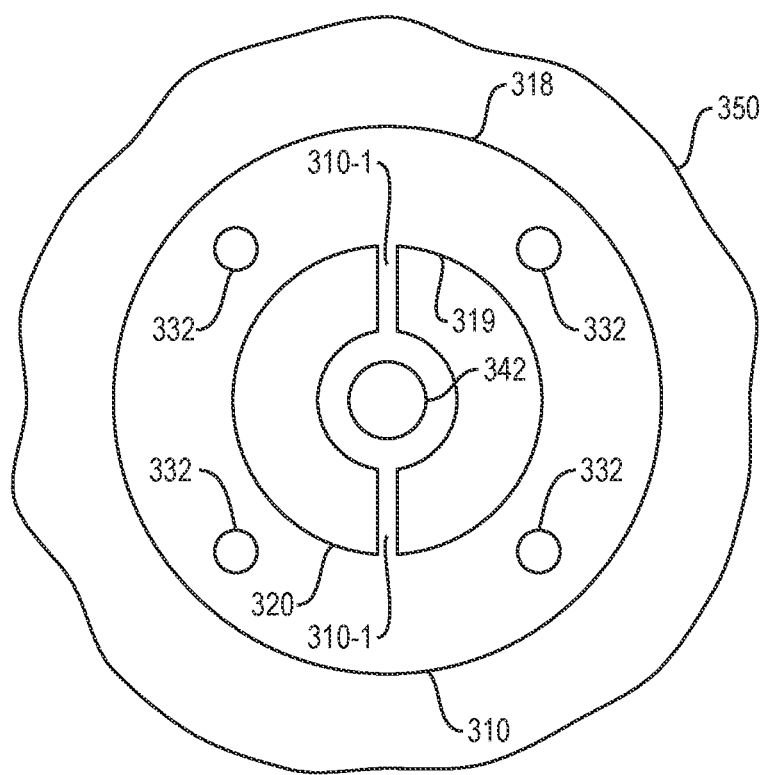
FIGS. 15A-15C show alternative configurations of the frame of FIGS. 11-14.
Figure 15B:
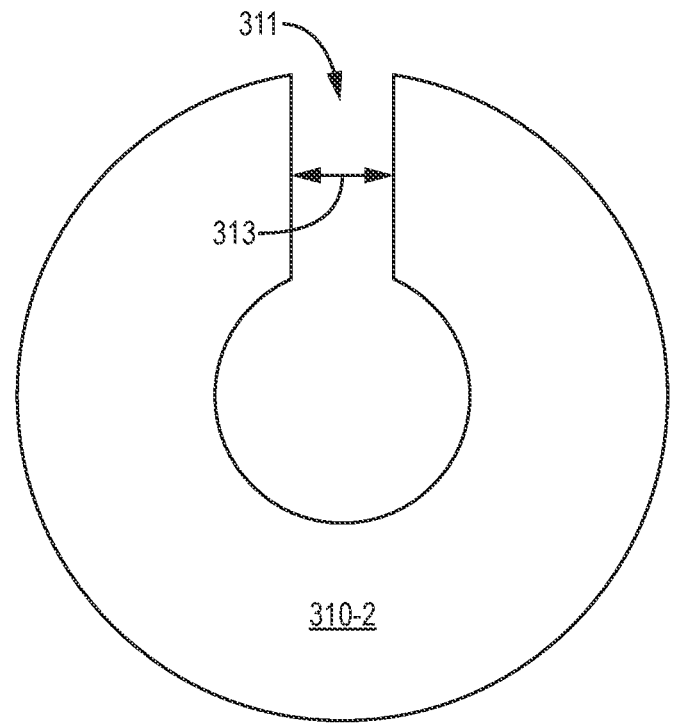
Figure 15C:
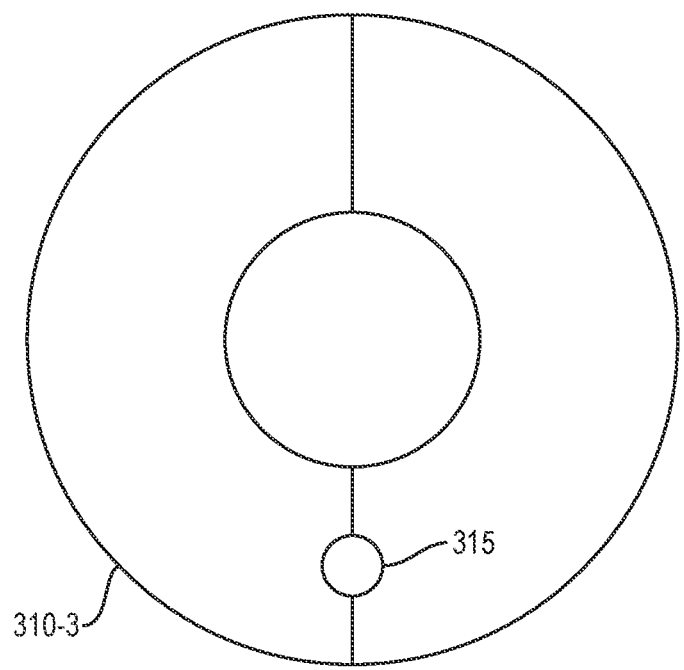

FIGS. 15A-15C show alternative configurations of the frame of FIGS. 11-14. Referring to FIGS. 11-15C, the circular frame 310 slidably engages the vessel 340 from a snug, resilient communication along the vessel 340. An insert of resilient or deformable material may occupy the void 220, and may include radial extensions 310-1 or spokes to accommodate any difference in diameter between the inner circumference 319 of the circular void 320 and the outer surface 342 of the vessel 340. Alternatively, the circular frame 310-2 may have a discontinuity 311 forming a gap 313 based on a diameter of the vessel 340. The gap 313 allows the frame 310-2 to slide over the vessel 340 so that the frame 310 may be applied after catheter insertion, rather than threading through a closed central void 320. Deformability of the circular frame 310 may allow a twisting or stretching deformation for forming the gap 313. Still further, FIG. 15C shows a hinged frame 310-3 where a hinge 315 allows articulation of two halves for opening and clamping around the vessel 340. These and other extensions may be performed for aligning the circular void 320 and any buffering material with the outer surface 342 of the vessel 340 based on the vessel diameter.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. An antimicrobial light-emitting device, comprising:
an illumination source configured around a urinary catheter defined by a tube with an axis therethrough for directing safe, antimicrobial light at the urethral meatus, further comprising:
a slidable cuff defined by a circular frame having a central void, disposed axially around the urinary catheter for positioning at the urinary catheter entry site at the urethral meatus, the circular frame having a surface extending perpendicular to the catheter and extending radially greater than an axial thickness along the urinary catheter; and
the illumination source including at least one LED arranged on the surface and focused axially along a length of the catheter for directing antimicrobial light around the urinary catheter towards the urethral meatus.

2. The device of claim 1 wherein the light has the ability to eradicate pathogenic microorganisms without harming the patient.

3. The device of claim 1 wherein the illumination source includes one or more light emitting diodes (LEDs), each LED providing a safe, antimicrobial light.

4. The device of claim 3 further comprising a heat sink configured to dissipate heat from the LEDs enabling safe positioning adjacent to the urethral meatus.

5. The device of claim 1 wherein the illumination source is disposed for irradiation of the urethral meatus, distal urethra, and adjacent indwelling urinary catheter.

6. The device of claim 1 wherein there is a central void within the device adapted to engage a urinary catheter.

7. The device of claim 6 wherein the slidable cuff is configured to be positioned at the urinary catheter entry site at the urethral meatus.

8. The device of claim 1 wherein the device is attachable onto the urinary catheter.

9. The device of claim 1 wherein the circular frame is oriented circumferentially around the urinary catheter.

10. The device of claim 1 wherein the antimicrobial light has a wavelength of far UVC or visible blue light.

11. The device of claim 1, wherein:
the central void is adapted to receive a catheter, the illumination source disposed on the frame for directing light of a predetermined wavelength at the central void, further comprising:
a connection to a power supply for activating the illumination source.

12. The device of claim 11 wherein the illumination source is disposed for irradiation of a vessel passing through the central void.

13. The device of claim 12 wherein the slidable cuff attaches the circular frame in a slidable engagement with the vessel for disposing the circular frame adjacent an insertion site.

14. The device of claim 1 wherein the circular frame extends in a direction normal to the axis of the urinary catheter, the one or more LEDs disposed in the circular frame and focusing perpendicular to a surface of the circular frame and axially along the urinary catheter.

15. A method for reducing catheter-associated urinary tract infection risk, comprising:
engaging an antimicrobial light-emitting device around a urinary catheter, the catheter defined by a tube with an axis therethrough, the light emitting device having a slidable cuff defined by a circular frame with a central void, the circular frame having a surface extending perpendicular to the catheter and extending radially greater than an axial thickness along the urinary catheter;
positioning the light emitting device on the surface to direct safe, antimicrobial light at the urethral meatus, distal urethra, and adjacent indwelling urinary catheter; and
directing the antimicrobial light from at least one LED arranged on the surface and focused axially along a length of the catheter for providing circumferential antimicrobial light around the urinary catheter towards the urethral meatus.

16. The method of claim 15, further comprising:
forming the antimicrobial light-emitting device including the circular frame defining the slidable cuff;
engaging the circular frame with a vessel defining the urinary catheter, the central void for passage of the vessel and an illumination source for directing light of a predetermined therapeutic wavelength;
disposing the catheter at a treatment region by insertion in a urethral path;
adjusting a position of the circular frame adjacent the treatment region for illuminating an insertion site; and
energizing the illumination source for irradiating the treatment region with the light of the therapeutic wavelength.

17. An antimicrobial urinary catheter device comprising a circumferential configuration of safe, antimicrobial light around a urinary catheter defined by a tube with an axis therethrough and directed for disinfecting the distal urethra, urethral meatus, and adjacent indwelling urinary catheter, further comprising:
a slidable cuff defined by a circular frame having a central void, disposed axially around the urinary catheter for positioning at the urinary catheter entry site at the urethral meatus, the circular frame having a surface extending perpendicular to the catheter and extending radially greater than an axial thickness along the urinary catheter; and
the illumination source including at least one LED arranged on the surface and focused axially along a length of the catheter for directing antimicrobial light around the urinary catheter towards the urethral meatus.

18. A method for preventing catheter-associated urinary tract infections, comprising:
bathing a urinary catheter defined by a tube with an axis therethrough and an adjacent distal urethra and urethral meatus in safe, antimicrobial light, by:
directing the antimicrobial light from at least one LED arranged on a surface of a slidable cuff defined by a circular frame having a central void and engaged circumferentially around the urinary catheter for focusing axially along a length of the catheter for directing antimicrobial light around the urinary catheter towards the urethral meatus, the circular frame defining the surface, the surface extending perpendicular to the catheter and extending radially greater than an axial thickness along the urinary catheter.

* * * * *